United States Patent [19]

Cody et al.

[11] Patent Number: 4,993,264

[45] Date of Patent: Feb. 19, 1991

[54] PASSIVE ACOUSTICS PROCESS TO MONITOR FLUIDIZED BED LEVEL

[75] Inventors: George D. Cody, Princeton; Charles L. Baker, Morris Plains, both of N.J.; Eugene R. Elzinga, Jr., Marquette, Mich.

[73] Assignee: Exxon Research and Engineering Company, Florham Park, N.J.

[21] Appl. No.: 317,872

[22] Filed: Mar. 2, 1989

[51] Int. Cl.$^5$ .............................................. G01N 29/00
[52] U.S. Cl. ......................................... 73/579; 73/602
[58] Field of Search ................ 73/579, 602, 587, 590, 73/592, 584, 861.18, 861.21, 290 V; 201/1

[56] References Cited

U.S. PATENT DOCUMENTS 4,641,526  2/1987  Izumi et al. ............................ 73/587
4,824,016  4/1989  Cody et al. ......................... 73/861.18

FOREIGN PATENT DOCUMENTS

61-268287  5/1988  Japan ..................................... 73/579

Primary Examiner—Hezron E. Williams
Assistant Examiner—Louis M. Arana
Attorney, Agent, or Firm—Ronald D. Hantman

[57] ABSTRACT

A method for the non-intrusive determination of the bed level in two phase fluid bed reactor using wall vibrations of the reactor.

5 Claims, 9 Drawing Sheets

PASSIVE ACOUSTICS PROCESS TO MONITOR FLUIDIZED BED LEVEL

BACKGROUND OF THE INVENTION

A fluidized bed is a suspension of solid particles in a stream of gas or liquid of sufficient velocity to support the particle by flow forces against the downward force of gravity. Fluidized beds are critical components of important petrochemical processing units such as the catalytic cracking ("cat-cracking") of petroleum on catalytic particles to produce lighter and more valuable products as well as thermal cracking of heavy feeds on coke particles ("fluid bed cokers" or "flexi-cokers") to again produce lighter and more valuable feeds. In cat-cracking the regenerator where coke is burned off the catalyst to produce "fresh catalyst" contains a fluidized bed. The particles in the fluidized bed within the regenerator are approximately 60 micron diameter pellets of a zeolite. In the case of fluid bed or flexi-coking, fluidized beds can be found in the heater, reactor and in the case of flexi-coking, the gasifier. The particles in this case are approximately 100 to 150 micron particles of coke.

Other fluidized beds containing small solids suspended in a gas include advanced coal combustion units where small particles of coal are suspended and burned to produce heat with minimum pollution and maximum efficiency. Yet another example is found in separation processes in the chemical industry where a fine suspension of particles is suspended in a flowing liquid. In general, fluidized beds are used in many large scale processes where it is desired to maximize the interaction between the surface of a particle and a surrounding gas or liquid.

Fluidized beds can contain volume mass densities for the case of fluid bed cokers and regenerators of the order of 40 pounds per cubic foot and particle velocities of several feet per second. Fluidized beds of the order of 10 to 50 feet in diameter are found in coking and cat cracking. With bed heights of the order of 10 to 60 feet the contained fluids range from less than a hundred to more than a thousand tons of particles.

It is difficult to directly measure the bed height in these units because they are operated at high temperatures, usually have a refractory lining and the reactants tend to foul probes placed in the bed. As a result, the bed height is usually inferred from pressure drop measurements across the bed or from gamma ray absorption through the bed. The former is unreliable as discussed in detail in the following paragraph and the latter is a complex refinery safety problem.

The bed level (the height of the transition between the "dense" phase of the fluidized bed and the "dilute" phase) is an important variable in the overall process yield. This quantity is usually inferred from pressure drop measurements. The measurement is difficult for two reasons: the first is the above mentioned fact that the measurement itself is complicated by the possibility of fouling of the measurement tube and pressure artifacts by the bridge arrangement required to eliminate the pressure drop of the inert gas flow used to maintain the opening in the probe. A more fundamental reason is found in the inadequacy of the model used to infer bed level from pressure drop. The general principle is a relationship between the total weight of the bed and the pressure drop. For single phase fluid, where the fluid mass density is well known the connection is immediate and the fluid level is given by the pressure drop divided by the density of the fluid and the acceleration due to gravity. For the case of fluidized beds, the interpretation is less direct since the bed mass density may not be constant but may depend on flow conditions, such as the distribution of fluidization gas, or instabilities of the fluidized bed such as gas bubbling. There are many examples when bed heights have been so poorly monitored that conversion was adversely effected.

Accurate measurements of bed level in addition to monitoring agreement with design conditions, are often used as a diagnostic tool to determine fluidization failures such as "bed slump" where one side of the fluidized bed is not fluidized, or regions of excessive turbulence when fluidization gas is not distributed uniformly. In both cases the efficiency of the petrochemical process is greatly effected by the poor flow state of the contained two phase fluid. In the second case, the high particle velocity can lead to the loss of excessive fines into the atmosphere as well, or excessive temperature gradients within the bed. Finally if the bed height extends into the region of the vessel containing the cyclones, it can interfere with the proper functioning of the cyclones and produce excessive carry over of particles into the gas stream exiting the unit.

While pressure, temperature and net volume or mass flow are the normal way of monitoring the state of fluidization within a fluidized bed or while a unit is operating, there are a variety of techniques that can be brought to bear on functioning fluidized beds. One example is the use of gamma rays or neutrons to determine the mass density of particles within the vessel. This technique can only be used if the walls and/or diameter of the vessel are less than a critical value since the technique is based on deriving the density from absorption. Too large a vessel diameter, or too thick a wall drops the detected signal below the level of background noise and the mass density cannot be determined. In addition the presence of intense radioactive sources and the necessity to construct elaborate structure to support the detectors of the radiation reduce the use of this technology to elaborate field tests or where major uncertainties arise over the operation of the fluidized beds. The gamma or neutron technique is expensive, has to be scheduled in advance and usually beyond the capability of normal refinery personnel.

Non-intrusive probes that can be used to monitor the flow state of experimental fluidized beds would also be of great value in complementing visual, radiographic and radioactive tracer studies of flow in order to improve or modify existing designs, or for pilot plant studies. A current review of a wide variety of electrical, optical, thermal and mechanical technology for studying the hydrodynamics of experimental gas-solid fluidized beds is contained in a recent review by N. P. Cheremisonoff (Ind. Eng. Chem. Process Dev. 25, 329–351 (1986)). The review presents techniques that are "best suited for laboratory scale systems, [although] adaption to industrial pilot facilities and/or commercial units is possible in some cases". However, examination of the presented techniques suggest they suffer from the usual disadvantages of being intrusive, easily contaminated by the process or as in the case of so many of the radioactive techniques severely restricted by environmental or safety considerations.

In the July 1985 issue of the Journal of the American Society of Lubrication Engineers (Lubrication Engineering), J. W. Spencer and D. M. Stevens (of Babcock & Wilcox, a McDermott company of Lynchburg, Va.) describe a technique for "detecting and characterizing particulate matter in fluid flow systems" by using "acoustic emission technology". In this technology the impact of particles generates high frequency surface vibrational waves which are detected as "pulses" by resonant piezo electric transducers. As described in the article, only sensors in contact with probes inserted into the flowing stream correlated with bulk quantity or size of particles in the stream. Sensors mounted non-intrusively on the walls of the pipe "did not correlate well with probe-mounted transducers. Again this technique is intrusive since it requires penetration of the walls of the vessel (see also U.S. Pat. Nos. 3,816,773 and 4,095,474 which describe similarly intrusive techniques).

Thorough review of the prior art suggests that there are no known technologies for reliably and safely measuring or inferring the flow state of two phase flow within a fluidized bed that meet the following criteria:

(1) Non-intrusive and hence requiring neither penetration of the wall or the constructing of external frame works to support radioactive sources and detectors and hence permitting trouble shooting of commercial units;

(2) Non-radioactive and/or suitable for "on-line" monitoring of fluidized beds or transfer lines on working commercial units;

(3) Capable of applying in a "non-intrusive manner" to the refractory lined vessels and transfer lines containing solid particles in the presence of gases such as air, steam and/or volatile hydrocarbons with wall temperatures as high as 250° to 500° C.

SUMMARY OF THE INVENTION

The present invention is a method for the non-intrusive determination of the bed level in a two phase fluid bed in a structure for processing material (hereinafter referred to as a "reactor"). The method includes the following steps. Reactor wall vibrations are measured and then the power spectrum is determined as a function of frequency. The wall vibration measurements are taken at several positions along the reactor wall in the vertical direction. The area of the power spectrum under a resonance peak is determined for each of the positions. A change in the area of the power spectrum in the vertical direction is correlated with the be level.

The non-intrusive method permits the presence of internal refractory in the vessel containing the fluidized bed and can operate over wide extremes of temperature. It can be clearly distinguished from all active acoustic techniques and has a wider breadth of applications.

The process can be described as a "passive" process since the desired information is obtained from processing vibrational or solid borne sound produced by the process itself.

While the invention is of particular importance with respect to commercial units where there are few if any alternative technologies to directly monitor bed height, it will also find use in pilot plant and experimental studies. Although the description is focused on two phase solid/gas flow, the skilled practitioner will realize that it is also applicable to two phase solid/liquid flow.

BRIEF DESCRIPTION OF THE DRAWINGS

FIG. 3(A) shows the signal produced by accelerometer as a function of time, FIG. 3(B) shows the square of the signal produced by the accelerometer as a function of time and the relationship between the means square acceleration and the area under the power spectrum, and FIG. 3(C) shows the power spectrum as a function of frequency.

DESCRIPTION OF THE PREFERRED EMBODIMENT

The present invention is a passive acoustic process to monitor bed level in a fluid bed reactor. The process is intended to permit operation of the reactor under conditions that increase product yield or increase thermal efficiency or maintain performance over an extended period of time.

In order to utilize the invention, accelerometers are attached to the wall of the reactor vessel. The accelerometers 2 are placed vertically along the reactor wall from a reference point 4 near the bottom of the vessel, see FIG. 1.

Figure 1:
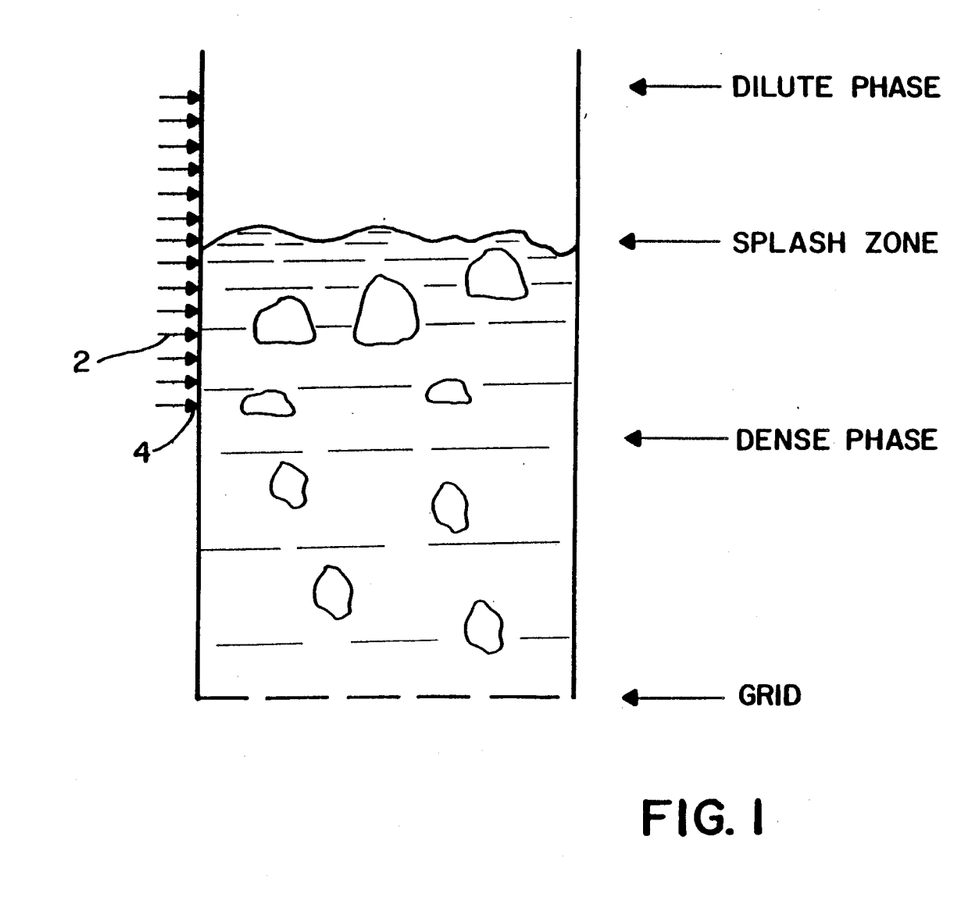
FIG. 1 shows a schematic of a fluidized bed in a reactor.

FIG. 1 shows a schematic of fluid bed reactor indicating the dense phase region of bed, the bed level as transition between dense phase and dilute phase, and the placement of accelerometers to precisely determine bed level.

Figure 2:
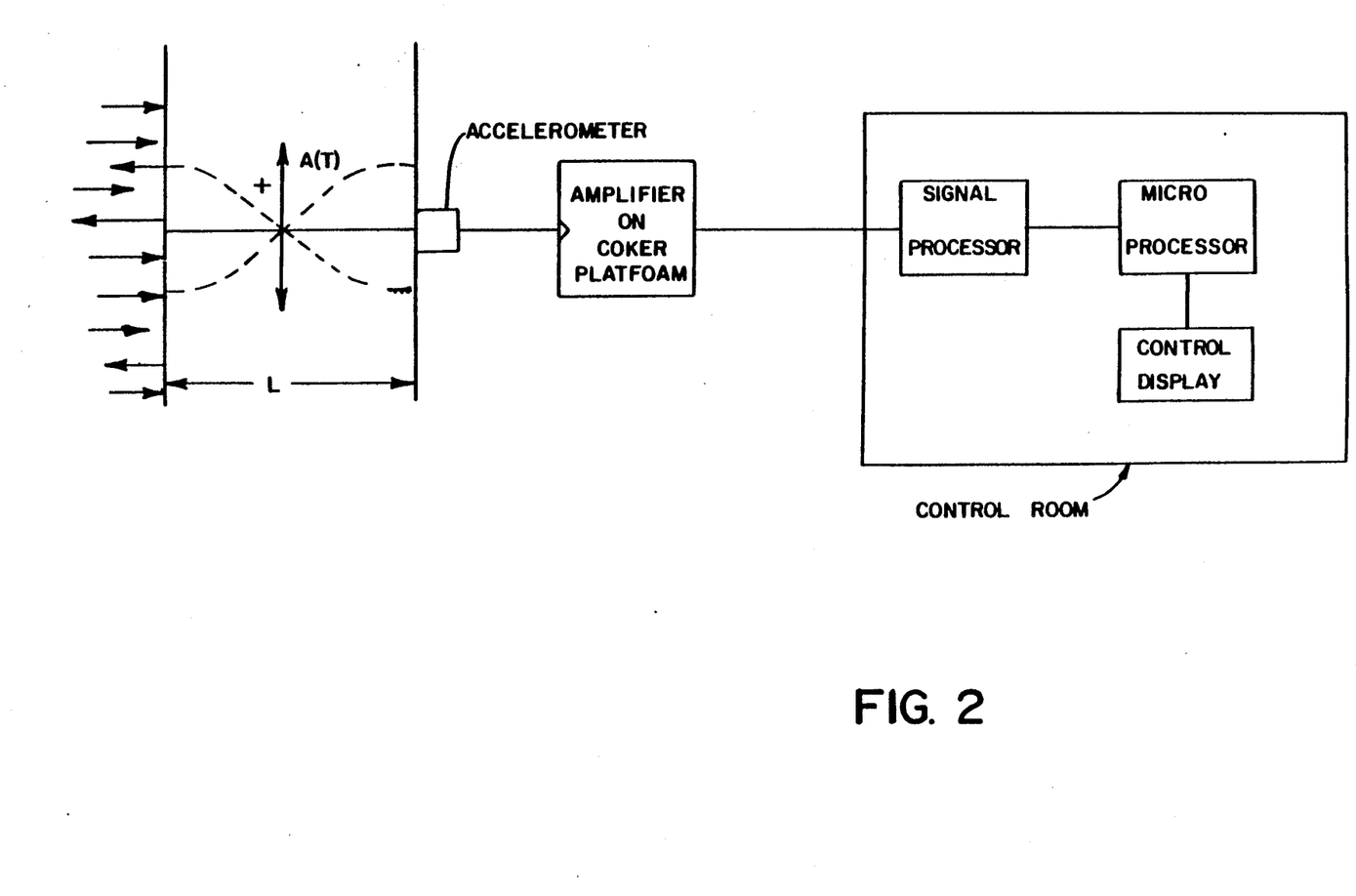
FIG. 2 shows a schematic showing the placement of a single accelerometer on the steel shell of a typical refractory lined vessel containing a fluidized bed reactor and its coupling to the amplifier and signal processor.
Figure 3A:
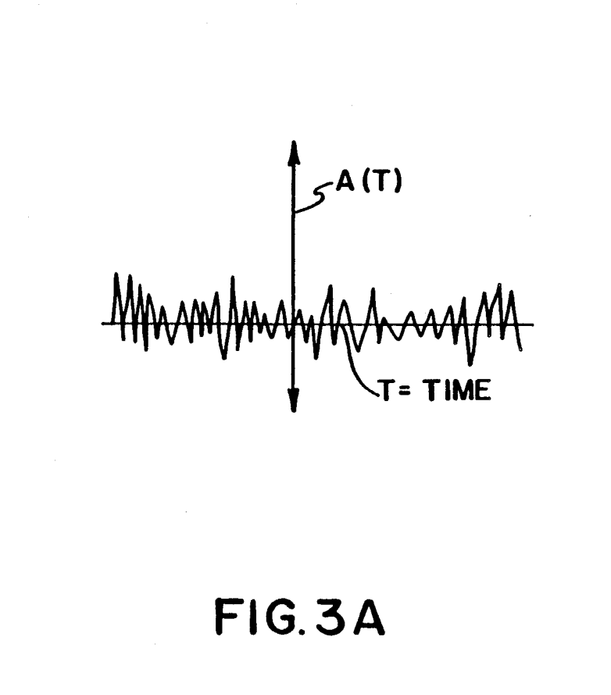
FIGS. 3A, 3B, and 3C illustrate the conversion of a time varying acceleration to a power spectrum.
Figure 3B:
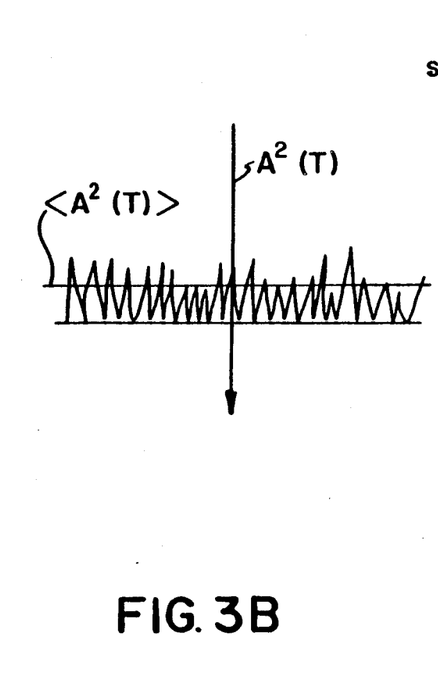
Figure 3C:
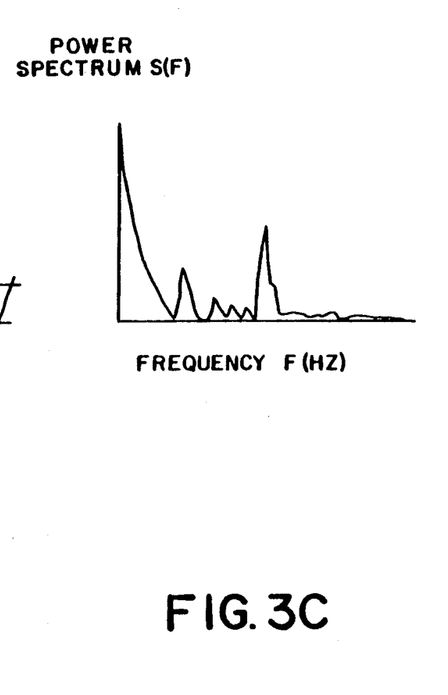

The electrical signal from the accelerometers, proportional to the wall's normal acceleration, is amplified and transmitted either by cable or optical link to a control room, FIG. 2. In the control room by suitable electronics, the power spectrum is determined as indicated in FIG. 3. The area under a certain peak of the power spectrum is then determined and is related to bed level in the reactor.

FIG. 2 shows a schematic diagram of how the measurement of wall acceleration is made. A magnetically (or otherwise) attached accelerometer (such as a B and K 4384) produces an electrical charge output proportional to the instantaneous acceleration of the wall. This charge is converted by a charge amplifier (such as a B and K 2635) to a voltage output which is again proportional to the normal acceleration of the wall. This voltage is processed by a signal processor (B and K 2032 or equivalent) to produce the power spectrum of the acceleration. The power spectrum of the acceleration of the wall exhibits a peak located at a frequency corresponding to the wall resonance. Both the frequency of this peak and its area can be determined by a suitable computer algorithm.

FIGS. 3A, 3B and 3C exhibit the relationship between the acceleration and its square as a function of time and as a function of frequency. The Power Spectrum for a stationary random function of time displays the mean square acceleration as a function of frequency. The area under the Power Spectrum is one half of the mean square acceleration.

Figure 4:
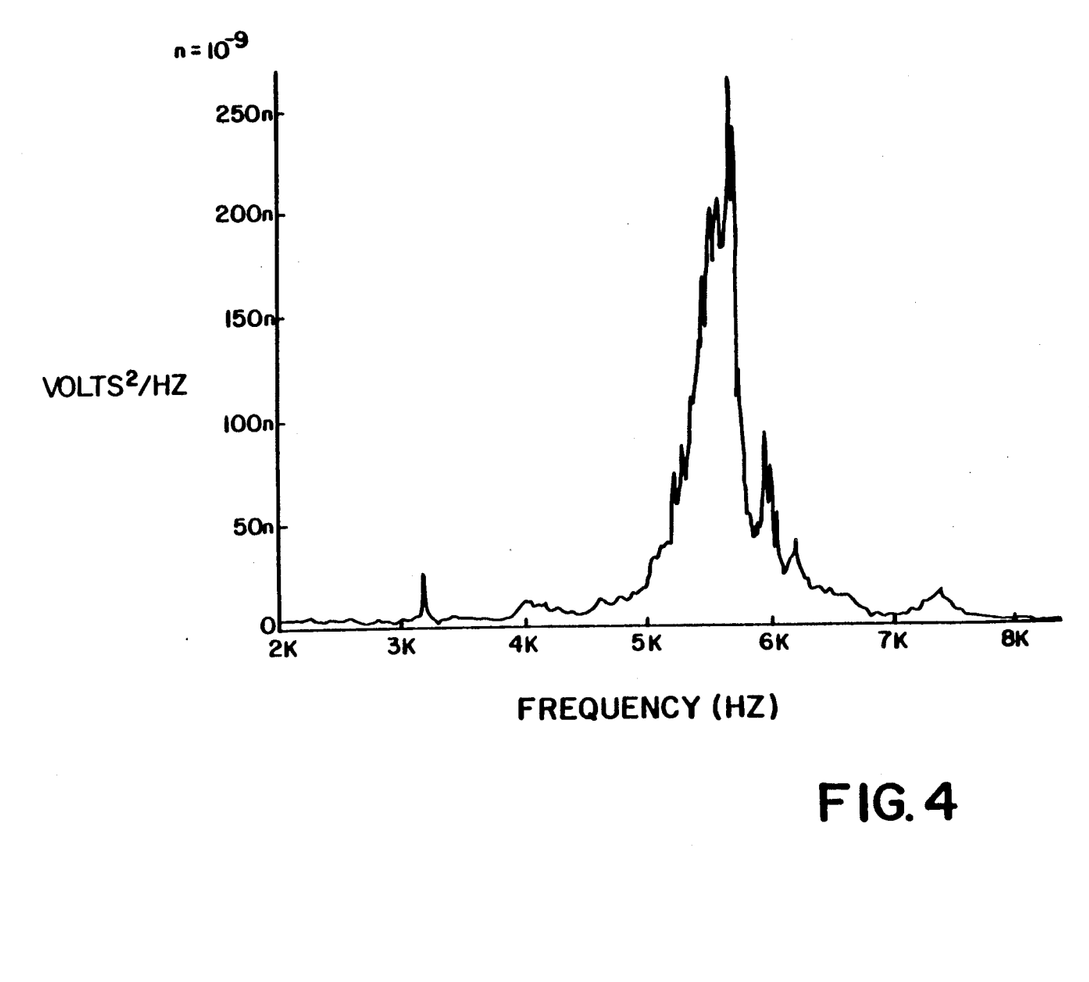
FIG. 4 shows a typical power spectrum from a refractory lined wall and illustrates the location of peak frequency and peak area.

FIG. 4 shows a typical power spectrum obtained from an accelerometer placed on a refractory lined wall on a fluid bed regenerator. The frequency and area of the wall resonance is indicated.

Figure 5:
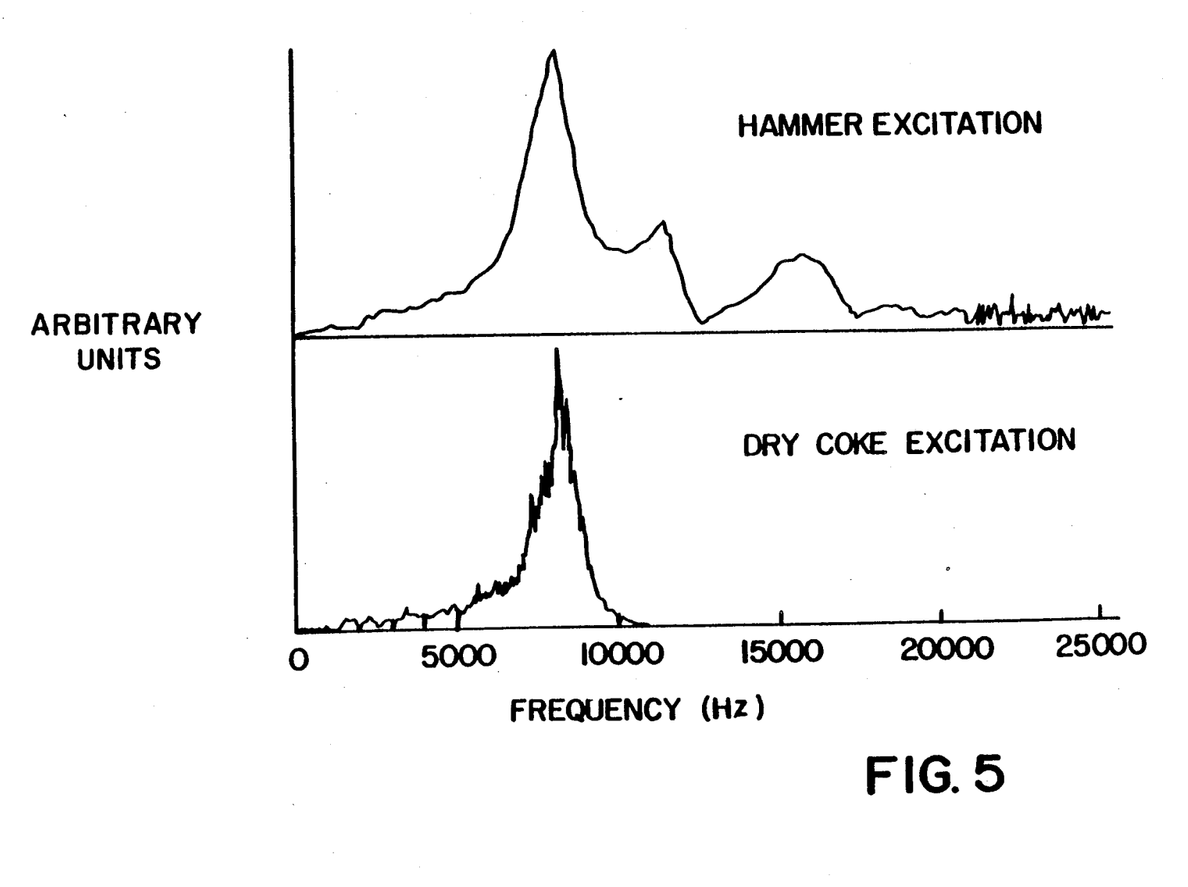
FIG. 5 shows the comparison between the response of the wall to hammer excitation and the response of the wall to particle excitation.

FIG. 2 also illustrates the placement of the accelerometer on the wall of the vessel containing the dense bed, and the spatial variation of the acceleration normal to the wall at the fundamental mode of wall vibration. Under these circumstances, for a homogeneous wall, bounded by two media whose density and sound velocity is much less than that of the wall, it is known that the fundamental mode has a node in the center and an antinode at the two boundaries. The frequency of the wall resonance is then simply given by the effective compressional sound velocity of the wall divided by twice the thickness of the wall. The frequency of the wall resonance can be determined directly by hammer excitation of the wall adjacent to the acceleration or by calculation. FIG. 2 also illustrates excitation of the wall resonance, namely the impact of the particles to the fluid bed which produces a steady state wall resonance peak in the power spectrum of the accelerometer output. FIG. 5 compares the wall resonance on the wall of a fluid bed coker excited by coke particle excitation and the wall resonance at the same location excited by hammer excitation. The frequency and shape of the resonance is the same.

The present invention is a method to monitor the bed level of a two phase fluidized bed by determining the power spectrum of the wall vibrations. Although the method does not depend on any particular theory, the method may be made plausible by relating the power spectrum to the characteristics of the particles within the unit.

In the present invention, the area of the localized wall resonance is used to obtain direct information on the state of the two phase fluid immediately adjacent to the wall. It can be shown that the area of the wall resonance, A, is given by $$A(M/S^2) = K_1[pB(1/CM^3)M^2(GM)V_o^3(FT/SEC)]^{\frac{1}{2}} \quad (1)$$

In Eq. (1) the area of the wall resonance A is defined in units of RMS acceleration and is easily obtained by integrating through the wall resonance as displayed in a power spectrum as shown in FIG. 4. The quantity $K_1$ is of the order of 10 to 15 for walls with steel of the order of 0.6" and refractory of the order of 5". The quantity $K_1$ can be independently determined by hammer excitation or if relative measurements are made preserved as a constant. The other quantities in Eq. (1) are:

pB = volume density of particles in units of number per cm³

M = average mass of a particle in units of grams $V_o$ = normal velocity of particles at wall in units of feet per second Eq. (1) is derived by considering the impact of solid particles within the two phase medium as the equivalent of a random impact of many hammers. It is the vibrational equivalent to the electrical phenomena of "shot noise". Equation (1) relates an easily measured quantity, A, to properties of the hydrodynamic state of the two phase fluid adjacent to the wall.

We can recast Eq. (1) in terms of particle diameter d and the mass density of the two phase fluid pM where $$pM = pB^M \quad (2)$$

With the substitution of Eq. (2) in Eq. (1) we obtain ($K_2$ is a constant of the order of $1-2\times10^{-6}$ for refractory walls approximately 5" thick lining steel walls approximately 0.5" thick and which again can be obtained by calibration under known flow conditions or by hammer excitation)

$$A(M/S^2) = K_2\{d(u)\}^{3/2}[pM(\#/FT^3)]^{\frac{1}{2}}V_o(FT/SEC)^{3/2} \quad (3)$$

where u is in microns and # is in lbs.

From Eq. (3), if we assume that d, the particle diameter is a constant, we see that the quantity A can be used to monitor pM or $V_o$.

The equations given above all relate the quantity A, which is measured by determining the area of the wall resonance, to significant features of the two phase flow within a fluidized bed. These include:

(1) From Eq. (1) and (3) we see that A is a function of the product $[pB(1/CM^3)M^2(GM)V_o^3(FT/SEC)]$. For conditions where M can be taken as a constant, a measurement of A can be obtained non-intrusively from an accelerometer attached to the wall of the vessel containing a fluidized bed. Displacing the accelerometer vertically, is a measure of $[pB(1/CM^3)V_o^3(FT/SEC)]$ at the wall within the vessel. This function varies considerably over the transition between the dense and dilute phase of the fluidized bed and we have found exhibits a signature at the transition corresponding to the bed level.

(2) The same method permits estimating the variation of the bed density, $pB(1/CM^3)$, through the dense phase if Vo may be considered constant. Significant differences in vertical surveys through the dense phase at different points around the circumference can be interpreted as variations in bed density through the dense bed.

An important feature of the invention is the ability to place an accelerometer on the steel shell of a refractory lined vessel and distinguish the wall resonance from other noise peaks and resonances. Distinguishing the wall resonance can be accomplished easily if it is the dominant peak, it falls at the frequency expected from prior knowledge of the thickness of the wall or by the use of hammer excitation (see FIG. 5). Once the wall resonance is identified in the power spectrum, its area determines the quantity A and can be used, as above to determine certain features of the state of the two phase fluid within the vessel. The constant KV can be determined by hammer measurements and the theory.

Important differences from the prior art are: (1) the fact that the measurement is non-intrusive requiring no modification or penetration of the vessel (fluffy outside insulation might have to be separated from the steel or other metal shell); (2) that it is passive, utilizing vibrational or acoustic noise generated within the process vessel or pipe, not externally generated sound or vibrations; (3) that the frequency range of the measurements is in the range imposed by the wall resonance, hence essentially low frequencies compared to those utilized in "ultrasonic" flow measurements. Another way of looking at this difference is that the wavelength of the vibrational measurements is of the order of the dimensions of the wall, whereas in ultrasonic measurements the wave length is considerably smaller than the dimension of the wall. Due to this observation the measurement process described in this patent is relatively immune to inhomegenities if the wall which would seriously effect any ultrasonic measurement.

EXAMPLE 1

Bed Level Determination of Fluidized Bed

The level was determined on a vessel containing a fluidized bed with the transition between the dense and dilute phases located at a height, H, above the "bottom" of the dense phase of the bed:

A reference accelerometer is attached to the unit at a location in the dense phase. The purpose of the reference is to monitor the general activity of the bed during the time of the measurements. An accelerometer is a commercial device whose output is a charge proportional to the acceleration of the wall (the second derivative of its displacement).

A vertical survey accelerometer is attached sequentially to the wall of the vessel containing the fluidized bed at locations below and above the reference accelerometer. If the locations are spaced about one foot apart in the region of the bed level satisfactory resolution is obtained.

The accelerometers are attached to the wall either by magnetic mounts or by studs cemented or welded to the wall of the unit at the above locations.

The output of the accelerometers is fed to "charge amplifiers" which are commercial devices whose output is a voltage proportional to the instantaneous acceleration of the location of the wall where the accelerometer is attached.

The wall resonance of the walls of such units is easily identified as a prominent peak in the power spectrum of the mean squared acceleration of the wall as measured by the output of a signal processor whose input are the above charge amplifiers. For fluid bed cokers and regenerators of catalytic cracking units, a common wall construction is 5 inches of refractory bonded to less than one inch of steel. For such walls the wall resonance is found between 5000 and 12000 Hz depending on the bonding of the refractory the steel as well as the compressional speed of sound in the refractory. In the power spectrum of the acceleration the wall resonance often exhibits itself as a predominant peak in the above frequency range. This fact is often sufficient for identification of the peak from other sources of noise. Alternatively the precise frequency of the wall resonance can be easily determined by calculation if the construction and acoustic properties of the wall are known, or experimentally by striking the wall with an impulse hammer and observing the response of the accelerometer as shown in FIG. 5.

From the power spectrum, the area of the wall resonance can be obtained by digital integration over its width, or can be determined by measuring the average power passed through a filter centered on the wall resonance with a width of a one to two thousand Hz.

The area of the wall resonance on the survey accelerometer is then divided by the area of the wall resonance on the reference accelerometer and its variation with vertical distance is displayed on a monitor screen. From the variation of this ratio, R, with distance or from the magnitude of the area itself, A, the position of the bed level at H, can be determined as a prominent peak in the spatial variation of the quantity, R or A.

Figure 6:
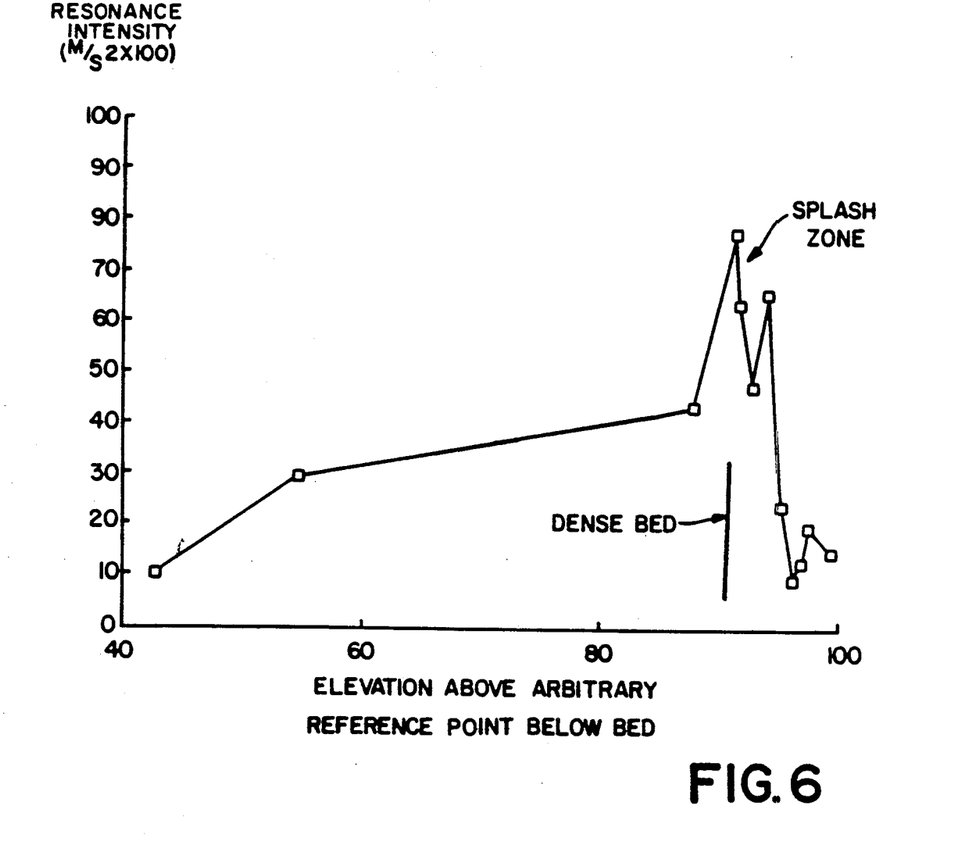
FIG. 6 shows the spatial variation in the vertical direction of RMS acceleration in wall resonance at a typical fluidized bed coker.

In FIG. 6 we show the spatial variation of the area of wall resonance, A, as a function of distance over the dense phase of a fluid bed coker. Over 50 feet there is only a gradual increase in the quantity, A, whereas over a five foot region in the region of the bed level, H, the signal rises rapidly and then falls by almost a factor of 7 from its peak value. This profile is characteristic of an increase in the particle flux to the wall of the unit in the vicinity of the top of the dense phase of the fluidized bed, due to the "splash zone" existing at the bed level H. From the figure it is seen that the bed height can be determined to about a foot uncertainty. The technique of using the spatial signature as an indication of the bed height was verified by raising the bed level by two feet and noting that the profile moved two feet. In addition, an absolute calculation of the bed height determined by the total pressure drop across the bed and assuming the bed density, agreed with a foot or so with the peak.

EXAMPLES 2

Bed Level Determination for Reactor Having Internal Structure

Figure 7A:
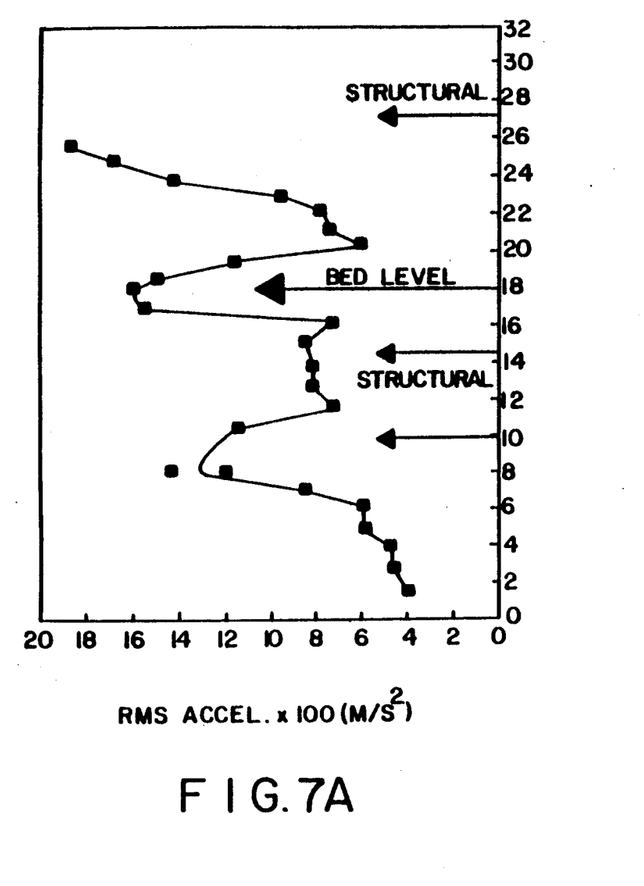
FIG. 7 shows spatial variation in the vertical direction of RMS acceleration in wall resonance of a fluidized bed coker having internal structure.
Figure 7B:
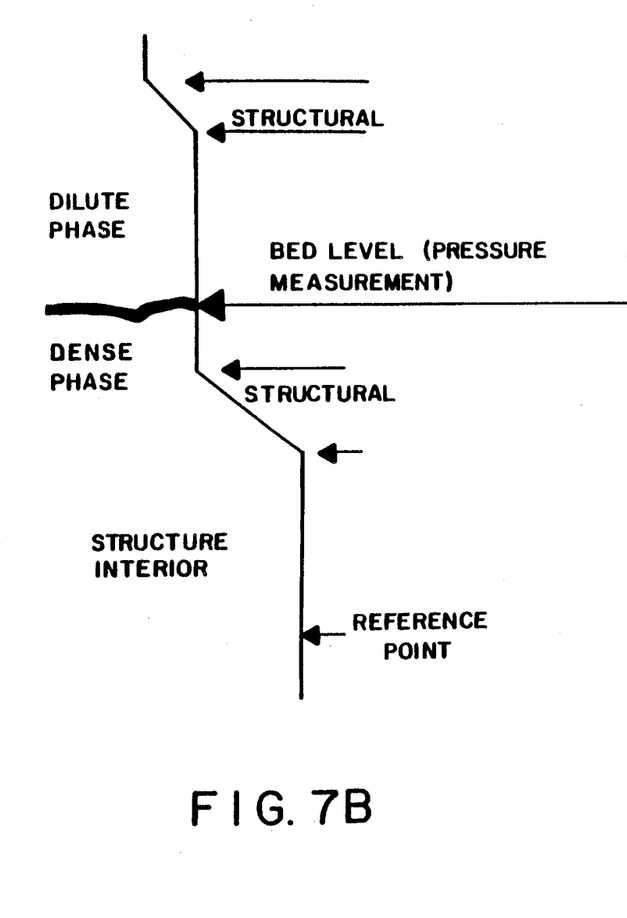
Figure 9:
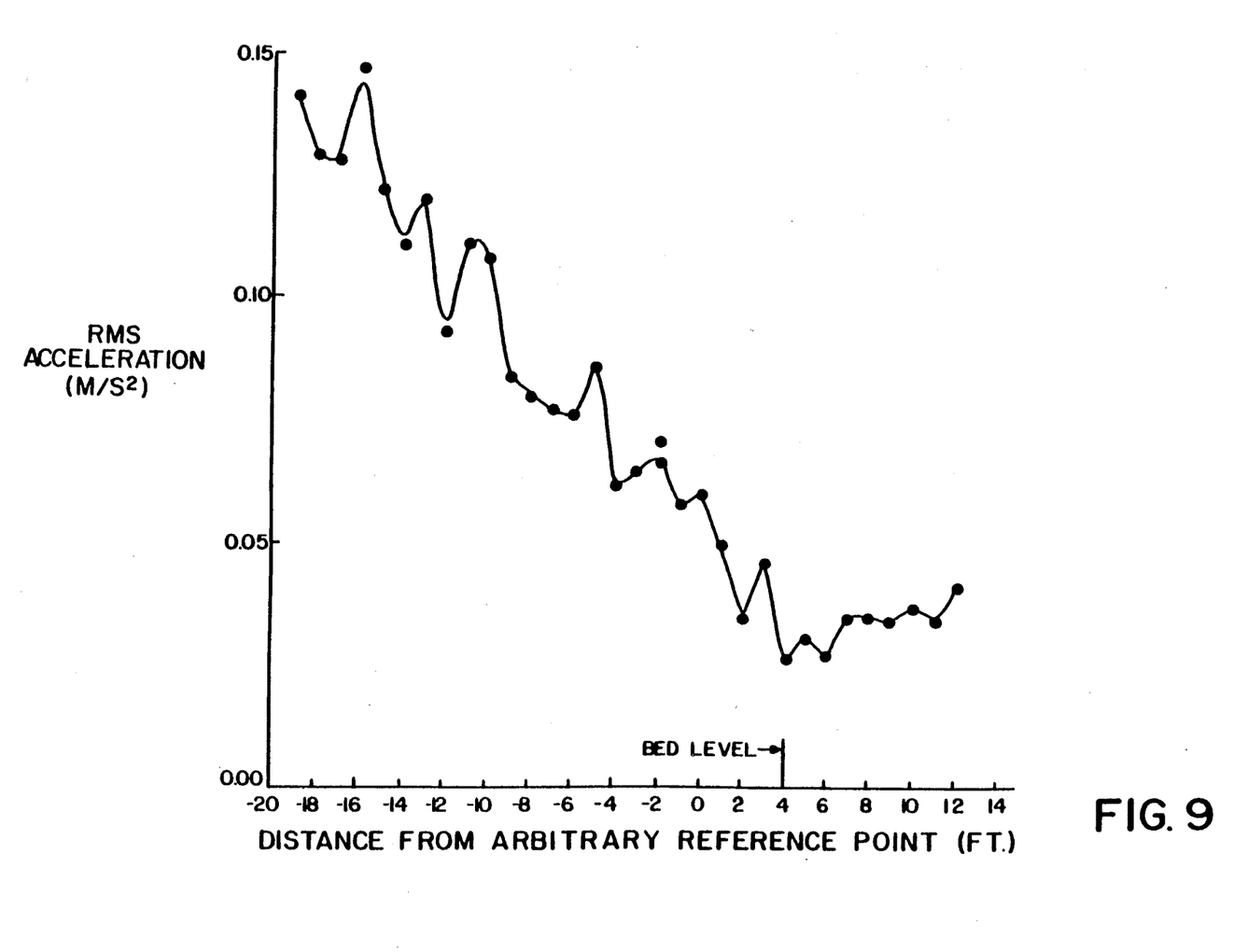
FIG. 9 shows a change of slope in spatial variation of the RMS acceleration in the wall resonance indicating the change in slope at the transition between the dense and dilute phases a cat cracker regenerator.

FIG. 7 gives an example of a power spectrum of coker reactor having internal structure. In this case the displayed vertical plot gives three spatial features. As shown in FIG. 9, two of the features, correspond to constrictions in the wall of the vessel and represent increased excitation of the wall resonance due to the geometrical constriction in vessel. As shown in FIG. 9, the middle peak falls in a region where the vessel is of uniform construction. Precise pressure drop measurements on the bed indicate that the bed level is precisely at the location of the middle peak at the time the vibrational measurements were made.

The previous examples were on fluidized beds containing particles with average particle diameter of 150 microns and bed densities of the order of 45 pounds per cubic foot. In both cases particles enter at the top of the dense phase entering through a side tube and are withdrawn from the bottom of the dense phase. In these and other examples for systems of similar design it was noted that the bed level could be identified as a signature in the spatial variation of either the quantity R or A, characterized by a peak over a relatively narrow spatial range. The identification of the peak with the bed level was based on precise pressure measurements and magnitudes for the bed density. It must be emphasized, as noted earlier, that accurate measurements of pressure are not always available due to fouling of the pressure indicators, and that the bed density is not known accurately under many operating conditions of the unit. Thus, the process described in the present invention meets a real need. However, conventional methods of determining bed level can be used to *calibrate* the vibrational technique described here.

EXAMPLE 3

Bed Level Determination in Regenerators on Fluid Catalytic Cracking Units

Fluidized beds are used in the regenerators of fluid catalytic cracking units (FCCU) to burn off the coke on the catalyst. There are several types of regenerators in present use. In some models, spent catalyst and air enter the regenerator through a grid and exit the regenerator through transfer lines well below bed level. In other models, spent catalyst enters the regenerator through a transfer line below bed level, and fresh catalyst exits at bed level. Air enters the catalyst through the grid. In other models, air enters through a grid, spent catalyst through a transfer line close to bed level and fresh catalyst exits the unit through a line below bed level. Schematics of such units can be found in *Petroleum Refining* J. H. Gary and G. E. Handwerk, Marcel Dekker, Inc. (1984).

Some regenerators have fluidized bed configurations similar to coker reactors and it the spatial signature exhibited by these units at the bed level is the same. There are no sources of combustion energy deep in the bed since the air input and the coked catalyst input are separated by the bed.

Figure 8:
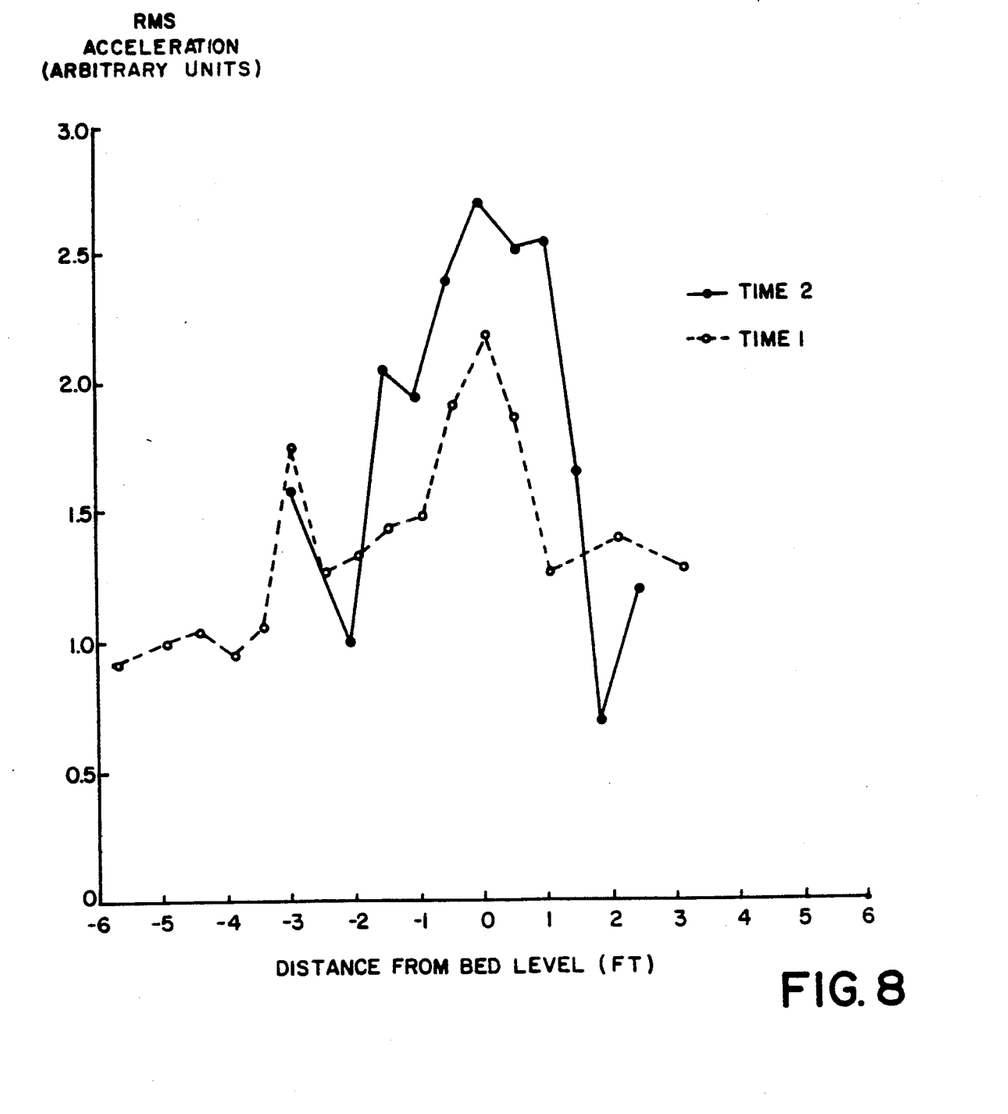
FIG. 8 shows a vertical survey of a typical cat cracker reactor where the air and spent catalyst are mixed prior to entry into the regenerator.

In models where air and spent catalyst are mixed prior to entry into the regenerator, the spatial signature of a vertical survey exhibits a peak at the bed level as shown in FIG. 8. The figure shows two curves measured at different times.

In regenerators where spent catalyst and air enter through adjacent intake transfer lines below bed level and fresh catalyst exits at bed level, combustion takes place in the bed and off axis. As might be expected, the spatial signature exhibited by a vertical survey of the regenerator is somewhat different from what has been exhibited. However, it is still sufficiently marked to distinguish the bed level. FIG. 9 exhibits the vertical variation of the RMS acceleration in the wall resonance on such a regenerator. For this unit the top of the fluidized bed is at 20 feet. In FIG. 9, the bed level is indicated by a change in the slope at 3 feet above the reference point.

From the present discussion it is clear that the sensitivity of the area of the wall resonance to the properties of the two phase fluid adjacent to the wall is sufficient to produce a signature in the plot of either the area of the wall resonance of a "survey accelerometer" or the ratio of the area of the wall resonance of the "survey accelerometer" to the area of the wall resonance of a reference accelerometer. Ambiguity in distinguishing the signature due to turbulence produced at the bed level—the "splash zone"—from constrictions in the vessel can be easily resolved by recourse to the detailed drawings of the unit, or by accurately measuring the pressure drop under circumstances when the density of the dense phase is known accurately, or by raising the height of the dense phase by lowering the rate of particle removal

What is claimed is:

1. A method for the non-intrusive determination of the bed level in a two phase fluidized bed in a structure for processing material comprising:
   (a) measuring wall vibrations of said structure and then determining the power spectrum as a function of frequency, said wall vibration measurements being taken at several positions along the structure wall in the vertical direction;
   (b) determining the area of the power spectrum which includes a resonance peak for each of said positions;
   (c) correlating a change in said area of the power spectrum in said vertical direction with said bed level.

2. The method of claim 1 wherein said structure is a fluid bed coker reactor.

3. The method of claim 1 wherein said structure is a fluidized bed catalytic cracker reactor.

4. The method of claim 1 wherein said structure is a regenerator.

5. The method of claim 1 wherein said step of measuring wall vibrations is performed by using an accelerometer.

* * * * *